United States Patent [19]

Gardella, Jr. et al.

[11] Patent Number: 4,946,903
[45] Date of Patent: Aug. 7, 1990

[54] OXYFLUOROPOLYMERS HAVING CHEMICALLY REACTIVE SURFACE FUNCTIONALITY AND INCREASED SURFACE ENERGIES

[75] Inventors: Joseph A. Gardella, Jr.; Terrance G. Vargo, both of Buffalo, N.Y.

[73] Assignee: The Research Foundation of State University of NY, Albany, N.Y.

[21] Appl. No.: 328,852

[22] Filed: Mar. 27, 1989

[51] Int. Cl.$^5$ .............................. C08F 8/26; C08F 8/00
[52] U.S. Cl. ............................... 525/326.4; 525/326.2; 525/338; 525/383; 525/384; 525/388; 204/168; 428/409
[58] Field of Search ................... 525/326.4, 326.2, 338, 525/388, 383, 384; 428/409; 204/168

[56] References Cited

U.S. PATENT DOCUMENTS

| | | | |
|---|---|---|---|
| 3,274,088 | 9/1966 | Wolinski | 204/165 |
| 3,274,089 | 9/1966 | Wolinski | 204/165 |
| 3,291,712 | 12/1966 | McBride | 204/165 |
| 3,296,011 | 1/1967 | McBride et al. | 117/47 |
| 3,676,181 | 7/1972 | Kowalewski | 117/47 A |
| 4,188,354 | 2/1980 | Monari et al. | 525/326.2 |
| 4,188,426 | 2/1980 | Auerback | 427/40 |
| 4,264,750 | 4/1981 | Anand et al. | 525/356 |
| 4,310,564 | 1/1982 | Imada et al. | 427/40 |
| 4,317,788 | 3/1982 | Imada et al. | 264/22 |
| 4,393,093 | 7/1983 | Sprout | 427/40 |
| 4,395,434 | 7/1983 | Imada et al. | 427/38 |
| 4,508,606 | 4/1985 | Andrade et al. | 204/165 |
| 4,548,769 | 10/1985 | Shimomura et al. | 264/22 |
| 4,548,867 | 10/1985 | Ueno et al. | 428/409 |
| 4,565,615 | 1/1986 | Radice | 204/168 |
| 4,718,907 | 1/1988 | Karwoski et al. | 623/12 |
| 4,735,996 | 4/1988 | Nagai et al. | 525/326.4 |

OTHER PUBLICATIONS

Vargo, Terrance et al., Polymer Preprints, vol. 28 (1), Apr. 1987.
Zisman, W. A., ACS Symposium Series 43, pp. 1-51, 1964.
Clark, D. T. et al., Journal of Polymer Science; Part A; Polymer Chemistry, vol. 25, 2643-2664 (1987).
Costello, Christine A. et al., Macromolecules, vol. 20 (11), 2819-2828 (1987), Chemical Engineering News (27), Sep. 22, 1986.
Dias, Anthony J., et al., Macromolecules, 1987, 20, 2068-2076.
Lee, Kang-Wook et al., Macromolecules, 1988, 21, 2318-2330.
Haque, Yasmeen et al., Journal of Applied Polymer Science, vol. 32, 4369-4381 (1986).
D'Agostino, Riccardo, J. Vac. Sci. Tech., A 3(6), Nov./Dec., 1985, 2627-2628.
Yasuda, H., et al., Journal of Polymer Science, Poly Chem. Ed., vol. 15, 991-1019 (1977).

Primary Examiner—Joseph L. Schofer
Assistant Examiner—Thomas McDonald, Jr.
Attorney, Agent, or Firm—Howard M. Ellis; Michael L. Dunn

[57] ABSTRACT

Through radio frequency glow discharge the molecular structure of a fluoropolymer is permanently modified by the substitution of hydrogen and oxygen or oxygen-containing radicals for fluorine to a depth of up to 100 Å. The surface morphological properties on a molecular level (e.g., pore structure) of the modified fluoropolymer remain substantially unchanged from those of the starting polymer as well as the bulk structure below the modified surface region while wettability with respect to low surface tension liquids and surface free energy as determined through critical surface tension are increased and new chemically reactive sites are created for further wet chemical modification or attachment of various functionality for development of a bioprobe device.

23 Claims, No Drawings

OXYFLUOROPOLYMERS HAVING CHEMICALLY REACTIVE SURFACE FUNCTIONALITY AND INCREASED SURFACE ENERGIES

BACKGROUND OF THE INVENTION

The present invention relates generally to novel fluoropolymers, and more specifically, to fluoropolymers, methods of making and articles manufactured therefrom, which fluoropolymers have been permanently modified at the molecular level but without altering the materials original surface morphologies as well as bulk characteristics.

Fluorinated polymers, such as fluorohydrocarbon polymers, e.g., polyvinylidene fluoride, polyvinyl fluoride (PVF), including the well-known fluorocarbon polymers, e.g., perfluorinated materials, such as PTFE, are characterized by extreme inertness, high thermal stability, hydrophobicity, and a low coefficient of friction as to resist adhesion to almost any material. While these properties are highly desirable, it would also be advantageous to modify some of the polymers' characteristics in order to expand the scope of their useful applications. For instance, in the field of biocompatible materials fluorocarbon polymers in various forms have been developed, but because of their chemical inertness and extremely low reactivity the scope of these improved devices, such as implantable prosthetic devices and probes has been limited. In the field of membranes and filters, fluoropolymers have also had limited applications due to low surface energy problems associated with these materials. Membranes and filters fabricated from PTFE, for example, are unable to selectively inhibit permeation of liquids with high surface tensions (>50 dynes/cm) while allowing liquids having lower surface tensions to pass through. PTFE has also been under intense study for applications in cell culture growth membranes, but a principal shortcoming has been the inability of cells to adhere to this low energy material.

Efforts of others to modify the properties of fluoropolymers have not been totally satisfactory. U.S. Pat. No. 4,548,867 (Ueno et al), for example, discloses a fluorine-containing synthetic resin having improved surface properties as evidenced by increased wettability with water, printability and susceptibility to adhesive bonding. The fluoropolymer is exposed to a low temperature plasma comprising an organic nitrogen-containing gas. Instead of modifying the atomic composition of the fluoropolymer starting material, Ueno et al form a thin "layer" of a nitrogen-containing wettable material thereto. Consequently, the adherence of such an overcoating tends to alter the microstructural morphology of the original polymer, especially with respect to pore size. This coating also alters desirable surface properties exhibited by the original fluorinated material.

Others have attempted the use of glow discharge and corona treatments to produce surface modifications. In some early work, Schonhorn and Hansen found that exposure of polyolefins and perfluorinated polymers to low power radio frequency electrodeless discharges in inert gas atmospheres produced favorable results over wet chemical methods. Their improvement in the bondability of surfaces was limited and attributed to the formation of a highly cross-linked surface layer. Studies of Hollahan et al, *J. Polym. Sci.*, 13, 807 (1969) aimed at rendering polymer surfaces biocompatible included the interaction of PTFE with plasmas excited in ammonia and nitrogen/hydrogen mixtures, the goal being the introduction of amino groups into the polymer surface. However, the long exposure times and high powers employed provided only limited results, and further, are thought to have produced significant changes not only in the surface chemistry, but also the native bulk properties. Morphology of the surface was also severely effected.

In another ESCA study entitled "ESCA Study of Polymer Surfaces Treated by Plasma," Yasuda et al, *J. Polym. Sci.*, Polym. Chem. Ed., 15, 991 (1977) the effects of discharges in argon and nitrogen on surface chemistry were considered on a range of polymers. PTFE was found to be particularly susceptible to defluorination and the introduction of oxygen and nitrogen moieties into the surface. Accordingly, there is need for permanently modified fluorinated polymers in which some of the original fluorine functionality is eliminated and replaced with oxygen functionality and hydrogen bonded to the carbon polymer backbone without the formation of coatings or layers while substantially preserving the original surface morphology and bulk characteristics of the unmodified material on a molecular scale.

SUMMARY OF THE INVENTION

It is a principal object of the invention to provide for novel oxyfluoropolymers in which the atomic structure of the native fluoropolymer material is permanently modified by the elimination of some of the original fluorine functionality and the introduction of both oxygen atoms or oxygen-containing groups and hydrogen atoms covalently bonded to the original carbon polymer backbone. The morphological properties of the oxyfluoropolymers at a molecular level remain substantially unchanged from those of the starting fluoropolymer materials while wettability with respect to low surface tension liquids and surface free energy ($\gamma_s$) as determined through critical surface tension ($\gamma_c$) are increased. The fluoropolymer starting material used in preparation of the oxyfluoropolymers is intended to include fluorocarbon type polymers and fluorohydrocarbon polymers.

More specifically, it is an object of the invention to provide for novel oxyfluoropolymers having increased surface energies in which a portion of the surface fluorine atoms to depths of about 10 to about 100 Å of a fluoropolymer starting material are permanently substituted with hydrogen atoms, and from about 5 to about 20% of the fluorine atoms are also substituted with oxygen functionality. That is, instead of introducing a modified polymer coating to the original material, the object is to provide for oxyfluoropolymers in which the original starting material is permanently modified at the molecular level by removal of some of the fluorine so the carbon backbone has fluorine, oxygen and hydrogen atoms covalently bonded thereto. In essence, the fluoropolymer starting material has a sufficient number of fluorine atoms permanently substituted with both hydrogen atoms and oxygen functionality covalently bonded to the carbon backbone to a surface depth of about 10 to about 100 Å to increase the surface free energy ($\gamma_s$) as determined through critical surface tension ($\gamma_c$).

It is a further object of the invention to provide for oxyfluoropolymers in which up to 98 percent, and more specifically, from about 20 to about 85 percent of the surface fluorine atoms to depths from 10 to about 100 Å are permanently substituted with hydrogen and oxygen and/or oxygen-containing groups of which from about 3 to about 30 percent of the substituted fluorine is replaced with oxygen or oxygen-containing groups and from about 70 to about 97 percent is substituted with hydrogen atoms. The morphological properties and bulk properties of the oxyfluoropolymer remain substantially unchanged over the starting fluoropolymer material.

The permanently modified fluoropolymers have increased wettability and/or adhesiveness, as well as chemically reactive sites allowing for attachment of various chemical functionality to these normally inert surfaces, and as such have applications which make them especially adaptable for membrane applications, e.g., filtration membranes or other surface mediated processes, e.g., adhesion prevention or promotion; devices such as bioprobes coated with oxyfluoropolymers making them biocompatible while allowing specific ion permeability; expanded PTFE membranes especially in the field of cell culture growth membranes; and because of improved wettability properties implantable prosthetic devices, such as bone replacements, heart valves, and the like.

It is yet a further object of the invention to provide for methods of making permanently modified fluoropolymers having increased surface energy by the steps of:

(a) providing a starting fluoropolymer material;
(b) providing a gas/vapor plasma mixture comprising hydrogen and at least one member selected from the group consisting of water, methanol and formaldehyde; and
(c) contacting said fluoropolymer material with said plasma mixture while exposing said fluoropolymer to at least one radio frequency glow discharge for a sufficient period to increase the surface free energy ($\gamma_s$) by permanently substituting to a depth from about 10 to about 100 Å on the starting fluoropolymer, fluorine atoms with hydrogen atoms and from about 5 to about 20% of said fluorine atoms with oxygen functionality.

The methods impart surface wettability and/or adhesiveness properties as well as chemically reactive sites to the original fluoropolymer without materially effecting the materials original hydrophobic properties. Plasma gas/vapor mixture concentrations of hydrogen, water, methanol, and formaldehyde together with wattage or power of the glow discharge and pressure (vacuum) are variables which determine the depth of surface modifications, as well as the respective atomic concentrations of carbon, fluorine, hydrogen and oxygen making up the modified portion of the final polymer.

DETAILED DESCRIPTION OF THE INVENTION

Through radio frequency glow discharge the atomic structure of the top 10 to about 100 Å of a fluoropolymeric starting material can be permanently modified by substitution of a portion of the original fluorine functionality with oxygen or oxygen-containing groups and hydrogen covalently bonded directly to the carbon polymer backbone. By regulating amounts and ratios of carbon, fluorine, oxygen and hydrogen in the modified polymer, surface energy can be increased from that of the original material along with wettability and adhesiveness properties without materially altering the corresponding hydrophobic properties, or altering the polymers original surface morphology and bulk characteristics.

In preparing the oxyfluoropolymers, useful fluoropolymer starting materials include both fluorocarbon polymers and fluorohydrocarbon polymers. This would include fluoropolymers having a carbon backbone with atoms bonded thereto consisting of either fluorine or both fluorine and hydrogen provided that when hydrogen atoms are present fluorine shall also be present in a ratio of at least 1:3. Preferably, the fluoropolymers include materials having a critical surface tension ($\gamma_c$) ranging generally from about 15 to about 30 dynes/cm. Specific representative examples of useful low surface energy fluorocarbon polymers are the perfluorinated polymers polytetrafluoroethylene (PTFE), polymers of hexafluoropropylene and tetrafluoroethylene like fluorinated ethylene-propylene (FEP) copolymers, etc. Suitable low surface area fluorohydrocarbon starting polymers include resins like polytrifluoroethylene, poly(vinylidene fluoride) (PVDF), poly(vinyl fluoride), poly(vinyl difluoride) and the like.

The oxyfluoropolymer compositions are especially unique in that a controllable amount from about 1 to about 98% of the fluorine atoms of the starting polymer's surface interface are permanently removed and replaced with hydrogen atoms and with oxygen atoms or low molecular weight oxygen-containing functionalities, so that all substituents are covalently bonded directly to the carbon backbone polymer chain to a depth of about 100 Å. Oxygen functionality may take the form of oxo, hydroxyl, alkoxy, like methoxy, ethoxy and propoxy or R'—CO— or combinations thereof where R' is hydrogen or alkyl, and particularly $C_1$-$C_5$ lower alkyl, including methyl, ethyl, propyl, isopropyl, and so on. Accordingly, unlike the nitrogen-containing monolayers/surface overcoatings of U.S. Pat. No. 4,548,867 the intrinsic atomic composition of the above starting material is permanently modified to regulated surface depths ranging from about 10 to about 100 Å, providing a novel combination of properties, i.e., chemically reactive sites, greater surface wettability and free energy enhancement of fluorinated carbons and hydrocarbons while still substantially preserving the hydrophobic properties and microstructural morphology, e.g., membranous structure, pore size, surface roughness on a molecular scale, etc.

The oxyfluoropolymers produce a wide variety of surface free energy increases where, for example, a fluoropolymer like PTFE with a $\gamma_c$ of about 18 dynes/cm at 20° C. can be increased to about 40 dynes/cm to a depth of between 10 to 100 Å for increased wettability and other surface properties relating to the surface free energy of a material. Even with such increases in surface free energy the hydrophobic properties of the original material remain substantially intact. That is, the modified polymers of the invention having hydrogen, oxygen and fluorine functionalities are covalently bonded to the carbon polymer backbone will still inhibit permeation and wetting by liquids with high surface tensions, i.e., >50 dynes/cm like water and other similar polar solvents, but also being wettable by liquids having low surface tensions, i.e., <50 dynes/cm, such as blood plasma and other nonpolar organic solvents. This is quite unexpected because when the surface free energy of a polymer is increased one normally finds with the increase in wettability an equivalent decrease in the hydrophobic properties of the material. However, quite surprisingly with the increased surface energy of the oxyfluoropolymers of the present invention wettability is increased without the normally expected decrease in hydrophobicity from that of the original starting material.

The oxyfluoropolymers are prepared by a plasma treatment process in which the previously described fluoropolymers are exposed to a single or a series of relatively low power radio frequency glow discharges (RFGD). The target fluoropolymers generally can be in the form of a sheet, premolded or coated article, such as a porous PTFE membrane or filter, e.g., Goretex ®, where, for example, increased permeability of ions would be desirable without altering pore characteristics of the native material; a bioprobe of conventional design coated with Teflon ® or a molded, implantable prosthetic device where, for instance, it would be desirable to modify its adhesive and/or surface reactivity characteristics to blood platelet attachment.

Instead of a plasma treatment with purely a gas the radio frequency glow discharge is conducted in an atmosphere of a gas/vapor mixture at pressure vacuums of under 1,000 mTorr, and more preferably, from about 50 to 200 mTorr, and power loadings of less than or equal to 100 watts.

Although not wishing to be held to any precise mode of action, the primary mechanism of the plasma treatment process of the instant invention is believed to involve the transfer of energy to the gaseous ions directly to form charged ionized gas species, i.e., ion sputtering of the polymer at the gas-solid interface. The radio frequency glow discharge plasma gas ions become excited through direct energy transfer by bombarding the gas ions with electrons. Thus, by exposing the fluoropolymer material to either a single or a series of radio frequency glow discharge gas/vapor plasmas consisting of admixtures of hydrogen gas ranging from 20% to 99% by volume, and 1 to about 80% by volume of a vapor from liquids, such as water, methanol, formaldehyde and mixtures thereof, 1 to about 98% of the surface fluorine atoms are permanently removed in a controlled/regulated manner and replaced with oxygen atoms or low molecular weight oxygen-containing functionality along with hydrogen atoms. Although hydrogen is required, in all instances, by itself it is insufficient to introduce both hydrogen and oxygen moieties to the carbon polymer backbone. A nonpolymerizable vapor/$H_2$ mixture is necessary to introduce the required hydrogen and oxygen or functionalized oxygen moieties onto the fluoropolymer without disrupting surface morphology. Further, uses of pure gas mixtures, specifically $H_2/O_2$ show only limited results. Representative radio frequency glow discharge plasmas and operating conditions are provided in Table I below:

TABLE I

| Starting Material | RFGD Mix Composition | Pressure (mTorr) | Time (Min.) | Depth (Å) | CALCULATED ATOMIC RATIOS (ESCA) | | | |
|---|---|---|---|---|---|---|---|---|
| | | | | | C/O | C/F | F/O | Stoichiometry |
| Unmodified PTFE* | — | — | — | — | ∞ | 0.45 | ∞ | $C_2F_{2.3}$ |
| Unmodified PVDF | — | — | — | — | ∞ | 1.0 | ∞ | $C_1F_1$ |
| Modified PTFE | 2% (vol) $H_2O$/98% $H_2$ | 150 | 20 | 100 | 7.5 | 1.5 | 5.0 | $C_{15}F_{10}H_{18}O_2$ |
| Modified PTFE | 2% (vol) $H_2O$/98% $H_2$ | 200 | 10 | 100 | 8.6 | 0.91 | 9.7 | $C_{17}F_{19}H_{13}O_2$ |
| Modified PTFE | 20% (vol) Methanol vapor/80% $H_2$ | 150 | 30 | 100 | 3.0 | 1.5 | 2.0 | $C_6F_4H_6O_2$ |
| Modified PTFE | 20% (vol) Methanol vapor/80% $H_2$ | 200 | 5 | 100 | 9.3 | 2.0 | 4.7 | $C_{28}F_{14}H_{39}O_3$ |
| Modified PVDF | 2% (vol) $H_2O$/98% $H_2$ | 200 | 10 | 100 | 8.0 | 16.0 | 0.48 | $C_{16}F_1H_{29}O_2$ |

*Porous Goretex membrane

The following specific examples demonstrate the various aspects of this invention, however, it is to be understood that these examples are for illustrative purposes only, and do not purport to be wholly definitive as to conditions and scope.

EXAMPLE I

Part A

To prepare oxyfluoropolymers, using radio frequency glow discharge (RFGD) a model PDC-23g RF plasma chamber having a maximum output of 100 watts from Harrick Scientific Corp., Ossining, NY, was modified by adding an in-line VG Model MD 95 ultra high vacuum (UHV) leak valve before the inlet side of the glow discharge unit. The UHV leak valve provided precise control of the system pressure while also allowing smooth flow of vaporized liquids into the plasma reaction chamber. In addition, a diffusion pump in conjunction with a roughing pump was installed at the outlet of the plasma reaction chamber. Optionally, a liquid nitrogen trap can be installed between the RFGD unit and the diffusion pump to protect the pump from potentially damaging vapors. Hydrogen from a flow meter, and liquids, e.g., water, methanol, formaldehyde, etc., are bled by the UH vacuum release valve to the inductively coupled plasma reaction chamber.

Through use of the diffusion pump, a base pressure of about 5 mTorr was obtainable and employed before all glow discharge treatments to effectuate a clean experimental system. By ultrasonically extracting the samples in hexanes, all trace contaminants caused by backflow of pump oil was minimized. In addition, by ultrasonically cleaning the samples, low molecular weight and evanescent surface constituents were effectively removed. This permitted more accurate analysis of permanent surface functionalities introduced into the fluoropolymer through RFGD surface modification.

Part B

A sheet of porous PTFE (Goretex) measuring 10 cm × 5 cm × 1 mm was analyzed using high resolution (17.9 eV) electron spectroscopy for chemical analysis (ESCA) to establish the true atomic percentages of carbon and fluorine present in the sample prior to glow discharge treatment. Measured peak areas of the detected atoms (carbon and fluorine) using atomic sensitivity factors gave corrected atomic percentages of 70% fluorine and 30% carbon for the sample corresponding to a $C_{1.0}F_{2.3}$ stoichiometry and a molecular structure $CF_3-(CF_2)-_n...-CF_3$. Corrected binding energies of the carbon and fluorine ls peaks indicated a totally saturated carbon backbone with no detectable oxygen.

The pure perfluorinated sheet was then placed on the sample stage in the plasma reaction chamber and exposed for 20 minutes at 100 watts to a gas/vapor RFGD plasma mixture consisting of ca. 98% by volume hydrogen and ca. 2% by volume water at 150 mTorr pressure. The sample was then subjected to ESCA analysis. The low and high resolution surveys showed C ls, F ls and O ls results indicating the molecular structure. C ls indicated the incorporation of large amounts of aliphatic C—H and —$CH_2$—$CH_2$— functionality with lesser amounts of carbon-oxygen functionality. Elemental analysis showed C 33.3%; F 22.2%; H 40.0%; O 4.5%. ATR —Infrared spectroscopic results indicated the formation of both C—O and —OH functionality.

EXAMPLE II

A second sample of the same pure porous PTFE sheet of Example I, Part B and of the same dimensions was exposed to a gas/vapor RFGD plasma mixture also consisting of 98% by volume hydrogen and 2% by volume water at 100 watts and a pressure of 200 mTorr like that of Example I, Part B. However, the exposure time was decreased from 20 to 10 minutes. The ESCA low resolution survey and high resolution C ls, F ls, and O ls spectra showed the addition of oxygen and hydrogen to the molecular structure of the PTFE surface. An ATR-IR spectrum of this material also indicated incorporation of amounts of C—O and —OH functionality onto the surface portion of the sheet. Elemental analysis showed C 33.3%; F 37.3%; H 25.5%; O 3.9%.

EXAMPLE III

A sheet of shear porous PTFE (Goretex) like that used in Examples I and II was exposed to a gas/vapor RFGD plasma mixture using the laboratory set-up described above in Part A of Example I. The plasma consisted of 80% by volume hydrogen and 20% by volume methanol. Exposure time was 30 minutes at a pressure of 150 mTorr. The ESCA low resolution and high resolution C ls, F ls, O ls spectra showed the introduction of oxygen at the molecular level on the PTFE surface. The C ls ESCA spectrum indicated both aliphatic carbon and C—O functionality with a corresponding decrease in fluorinated carbon groups. The F ls spectrum showed a large increase in peak width, indicative of two types of fluorine functional group environments residing at the PTFE surface region. The amount of oxygen functionality present in the modified oxyfluoropolymer surface was more than double that of the samples prepared in Examples I and II, as shown by the following elemental analysis: C 33.3%; F 22.0%; H 33.3%; O 11.1%. ATR-IR showed a corresponding increase in C—O and —OH functionality.

EXAMPLE IV

A sheet of poly(vinyl difluoride) (PVDF) measuring 10 cm × 5 cm × 1 mm was analyzed using high resolution ESCA to establish the composition of the sample. Two peaks of almost equal area were observed which were indicative of a molecular structure containing equal amounts of $CH_2$ and $CF_2$ groups. The unmodified polymer can be described stoichiometrically as $C_{1.0}F_{1.0}H_{1.0}$ with a molecular structure of $(CH_2-CF_2)_n$—. The unmodified PVDF sheet had an elemental analysis of C 33%; F 33%; H 33%.

The sample sheet of PVDF was exposed to a gas/vapor RFGD plasma mixture for 10 minutes at a pressure of 200 mTorr at 100 watts in the laboratory set up of Example I, Part A. The gas/vapor mixture consisted of 2% by volume water and 98% by volume hydrogen. The treated sample was then analyzed using ESCA low resolution survey and high resolution C ls, F ls and O ls which demonstrated an extreme drop in the fluorine signal with a corresponding increase in hydrogen and oxygen to the top surface to a depth of about 100 Å. The C ls spectrum indicated a hydrocarbon surface with some C—O functionality and little or no C—F functionality in the topmost 100 Å of the PVDF surface. ESCA analysis indicated only 2 atomic percent fluorine in the upper most 100 Å of the modified material whereas the original unmodified sheet contained 33 atomic percent fluorine. Elemental analysis of the treated PVDF was C 33.3%; F 2.1%; H 60.4%; O 4.2%.

EXAMPLE V

A sample of the same pure PTFE used in Example I, Part B, was exposed to a gas/vapor RFGD plasma mixture consisting of about 60% by volume hydrogen and 40% formaldehyde for 5 minutes at a pressure of 200 mTorr at 100 watts in the laboratory set-up of Example I, Part A. Elemental analysis by ESCA of the treated PTFE was found to be C 33.3%; F 16.7%; H 46.4%; O 3.6%. ATR-IR again indicated formation of C—O and —OH functionality.

EXAMPLE VI

Modified fluoropolymer materials (Table II below) were analyzed using a wettability profile which measures the contact angles of various liquids each having a different surface tension. This series of liquids with different surface tensions allows for the measurement of changes in wettability as related to an empirical measure of surface energy. Further, the change in hydrophilicity/hydrophobicity can also be measured through use of the higher surface tension polar liquids (i.e., water and glycerol). The critical surface tension ($\gamma_c$) is the value given indicating the surface tension of the liquid which totally spreads on the surface in question. Liquids with surface tensions equal to or below this value will also be observed to spread, and thus, increases in $\gamma_c$ relate an increase in surface energy allowing for greater wettability of liquids with higher surface tensions.

The contact angles of the various liquids listed in Table II were measured on each respective material employing a model 100 Rame' Hart Goniometer for measuring the angle and a freshly flamed Pt wire for placing the purified liquid drops on the material surfaces.

TABLE II

| | LIQUID/VAPOR SURFACE TENSIONS (dyne/cm) | Measured Contact Angles (degrees) | | | |
|---|---|---|---|---|---|
| | | UNMODIFIED PTFE GORTEX | MODIFIED PTFE 20 min $H_2(H_2O)$ EXAMPLE II | UNMODIFIED PVDF | MODIFIED PVDF 10 min $H_2(H_2O)$ EXAMPLE IV |
| Water | 72.4 | ~140° | 110° | 120° | 110° |
| Glycerol | 64.8 | 130° | 115° | 125° | 115° |
| Formamide | 58.9 | 130° | 112° | 115° | 95° |
| Thiodiglycol | 53.5 | 125° | 120° | 107° | 80° |
| Methylene Iodide | 49.0 | 120° | 115° | 102° | 25° |
| 1-Bromo-Naphthalene | 45.0 | 100° | 110° | 40° | 10° |
| 1-Methyl-Naphthalene | 39.3 | 100° | 90° | 10° | (spread) 0° |
| Dicyclohexyl | 32.7 | 93° | 60° | 10 | 0° |
| n-Hexadecane | 27.6 | 20° | (spread) 0° | 5° | 0° |
| n-Tridecane | 26.0 | 10° | 0° | (spread) 0° | 0° |
| n-Decane | 23.8 | (spread) 0° | 0° | 0° | 0° |

Table II shows that a decrease in contact angles as measured on the 20 minute $H_2/H_2O$ RFGD modified Goretex was small for the liquids having surface tensions >39.3 dyne/cm indicating a retention of the original materials non-wetting characteristics for these liquids. The measured angles for these liquids also indicate the retention of surface residing fluorine functionality and especially a large degree of hydrophobicity as indicated from the angles measured for water and glycerol. Below 39.3 dyne/cm, the contact angles of the utilized liquids showed a larger degree of wettability indicating an increase in surface energy which is ascribed to the presence of small amounts of surface residing oxygen functionality earlier detected by ESCA and IR results. A 0° measurement (i.e., $\gamma_c$) was observed at 27.6 dyne/cm for the $H_2/H_2O$ RFGD modified Goretex as compared to 23.8 dyne/cm as measured on the unmodified Goretex membrane. This indicates an increase in surface energy again, attributed to the creation of surface residing oxygen functionality in close proximity to the fluorine functionality.

Similar observation were made on the PVDF modified material except that the surface energy showed a greater degree of enhancement (i.e., $\gamma_c$ increased from 27.6 dyne/cm as measured on unmodified PVDF to 39.3 dyne/cm for the $H_2/H_2O$ RFGD modified PVDF). Again, the degree of hydrophobicity showed only minor decreases as indicated by >90° (110°) measured contact angle of water on the modified PVDF surface.

These two examples illustrate only two values for $\gamma_c$ of modified materials and measurements achieving a range of $\gamma_c$ values (from 25–40 dyne/cm have been observed for the Goretex modified materials and 30–40 dyne/cm for the modified PVDF materials) which are dependent on RFGD conditions especially hydrogen/vapor concentration and the liquid employed as the vapor.

EXAMPLE VII

A bio-probe may be fabricated for detecting various molecules or important species in a biological system, e.g., kidney. A very low surface energy fluoropolymer, such as porous PTFE, e.g., Goretex membrane, would be a suitable starting material where total inertness is desired. However, a bio-probe would be especially desirable in this instance if ion permeability was enhanced without changing the membrane's pore structure or hydrophobic character, and at the same time the majority of the probe would remain essentially inert and nonreactive so as to prevent contamination or bio-rejection when placed in vitro. This may be accomplished by the removal of fluorine atoms and the incorporation of —OH functionality into the PTFE. Other moieties may then be introduced by reacting with these sites. Silanes, for example, may be quickly reacted with such oxygen functionalities by formation of the Si—O bond. Accordingly, through known masking techniques several modified sites may be created by exposing the polymer to gas/vapor RFGD plasma mixtures as disclosed above. Furthermore, using known masking techniques each of the modified sites may be reacted with a silane having different chemical and/or physical characteristics. Each of these silanized sites would also be isolated from one another due to the unmodified inert PTFE material surrounding each site. The modified material would then be useful in fabricating the bia-probe.

The invention has been described in conjunction with specific examples thereof. This is illustrative only. Accordingly, many alternatives, modifications and variations will be apparent to those skilled in the art in light of the foregoing description, and it is therefore intended to embrace all such alternatives, modifications and variations as to fall within the spirit and broad scope of the appended claims.

What is claimed is:

1. An oxyfluoropolymer comprising a fluoropolymer in which up to about 98 percent of the surface fluorine atoms to depths from about 10 to about 100 Å are permanently substituted with hydrogen and oxygen or oxygen-containing groups of which from about 3 to about 30 percent of the substituted fluorine is replaced with oxygen or oxygen-containing groups and from about 70 to about 97 percent is substituted with hydrogen atoms, the morphological and hydrophobic properties of the oxyfluoropolymer remaining substantially unchanged from those of said fluoropolymer while wettability with respect to low surface tension liquids and surface free energy ($\gamma_s$) as determined through critical surface tension ($\gamma_c$) are increased.

2. The oxyfluoropolymer of claim 1 wherein the fluoropolymer is a fluorocarbon polymer or a fluorohydrocarbon polymer.

3. The oxyfluoropolymer of claim 2 wherein the fluoropolymer is a material having a $\gamma_c$ ranging from about 15 to about 30 dynes/cm.

4. The oxyfluoropolymer of claim 1 wherein the fluoropolymer is a fluorohydrocarbon polymer in which hydrogen and fluorine are present in a ratio of at least 1:3.

5. The oxyfluoropolymer of claim 4 wherein the oxygen-containing group is a member selected from the group consisting of hydroxyl, alkoxy, R'—CO— and combinations thereof and R' is hydrogen or alkyl.

6. The oxyfluoropolymer of claim 1 wherein the fluoropolymer is PTFE or PVDF.

7. The oxyfluoropolymer of claim 1 wherein from about 20 to about 85 percent of the surface fluorine atoms are substituted with hydrogen and oxygen or oxygen-containing groups.

8. An oxyfluoropolymer, which comprises a fluoropolymer having a carbon backbone with atoms bonded thereto selected from the group consisting of fluorine and both fluorine and hydrogen provided that when hydrogen atoms are present fluorine shall be present in a ratio of at least 1:3, said fluoropolymer having a sufficient number of fluorine atoms substituted with both hydrogen atoms and oxygen atoms or oxygen-containing radicals covalently bonded to said carbon backbone to a surface depth from about 10 to about 100 Å to increase the wettability with respect to low surface tension liquids and surface free energy ($\gamma_s$) as determined through critical surface tension ($\gamma_c$) while the hydrophobic properties of said oxyfluoropolymer remain substantially unchanged from those of the fluoropolymer.

9. The oxyfluoropolymer of claim 8 wherein the fluoropolymer is PTFE or PVDF.

10. The oxyfluoropolymer of claim 9 wherein the oxygen-containing radical is hydroxyl, alkoxy, R'—CO— or combinations thereof and R' is hydrogen or alkyl.

11. A method of making a permanently modified fluoropolymer having increased surface energy, which comprises the steps of:
   (a) providing a fluoropolymer;
   (b) providing a gas/vapor plasma mixture comprising hydrogen and at least one member selected from the group consisting of water, methanol and formaldehyde, and
   (c) contacting said fluoropolymer with said gas/vapor plasma mixture while exposing said fluoropolymer to at least one radio frequency glow discharge under vacuum for a sufficient period to substitute a portion of the fluorine atoms on the fluoropolymer to a depth of from about 10 to 100 Å with covalently bonded hydrogen and oxygen atoms or oxygen-containing radicals to increase the wettability of said fluoropolymer with respect to low surface tension liquids without substantial change to the morphological and hydrophobic properties.

12. The method of claim 11 in which up to about 98 percent of the surface fluorine atoms are substituted with hydrogen and oxygen or oxygen-containing groups of which from about 3 to about 30 percent of the substituted fluorine is replaced with oxygen or oxygen-containing groups and from about 70 to about 97 percent is substituted with hydrogen atoms, said oxygen-containing group being a member selected from the group consisting of hydroxyl, alkoxy, R'—CO— or combinations thereof, and R' is hydrogen or alkyl.

13. The method of claim 12 wherein the fluoropolymer is PTFE and the plasma gas/vapor mixture comprises hydrogen and methanol.

14. The method of claim 11 wherein the fluoropolymer is PTFE and the plasma gas/vapor mixture comprises hydrogen and water.

15. A bioprobe coated with the oxyfluoropolymer of claim 1.

16. A bioprobe coated with the oxyfluoropolymer of claim 6.

17. A bioprobe coated with the oxyfluoropolymer of claim 8.

18. A porous membrane comprising the oxyfluoropolymer of claim 1.

19. A porous membrane comprising the oxyfluoropolymer of claim 8.

20. An implantable prosthetic device comprising the oxyfluoropolymer of claim 1.

21. An implantable prosthetic device comprising the oxyfluoropolymer of claim 7.

22. A porous membrane comprising the oxyfluoropolymer of claim 6.

23. The porous membrane of claim 22 wherein the fluoropolymer is expanded PTFE.

* * * * *